US008900132B2

(12) United States Patent
Ishigami et al.

(10) Patent No.: US 8,900,132 B2
(45) Date of Patent: Dec. 2, 2014

(54) ENDOSCOPE APPARATUS

(75) Inventors: Takakazu Ishigami, Tokyo (JP); Ayumu Inada, Tokyo (JP)

(73) Assignee: Olympus Corporation, Tokyo (JP)

( * ) Notice: Subject to any disclaimer, the term of this patent is extended or adjusted under 35 U.S.C. 154(b) by 401 days.

(21) Appl. No.: 12/852,597

(22) Filed: Aug. 9, 2010

(65) Prior Publication Data

US 2011/0034773 A1 Feb. 10, 2011

(30) Foreign Application Priority Data

Aug. 10, 2009 (JP) ................................. 2009-185760

(51) Int. Cl.
| | |
|---|---|
| *A61B 1/06* | (2006.01) |
| *G02B 23/24* | (2006.01) |
| *A61B 1/00* | (2006.01) |
| *A61B 1/005* | (2006.01) |
| *A61B 1/12* | (2006.01) |

(52) U.S. Cl.
CPC ........ *A61B 1/00039* (2013.01); *G02B 23/2476* (2013.01); *A61B 1/00128* (2013.01); *A61B 1/00052* (2013.01); *A61B 1/0052* (2013.01); *A61B 1/0669* (2013.01); *A61B 1/128* (2013.01)
USPC ........... 600/131; 600/112; 600/114; 600/119; 600/121; 600/122; 600/123; 600/147; 600/172

(58) Field of Classification Search
CPC ........... A61B 1/00121; A61B 1/00126; A61B 1/00128; A61B 1/0052; A61B 1/0669
USPC ......... 600/112, 114, 119, 121–123, 131, 147, 600/172
See application file for complete search history.

(56) References Cited

U.S. PATENT DOCUMENTS 3,670,811 A * 6/1972 Christensen ................ 165/134.1
5,373,317 A 12/1994 Salvati et al.
(Continued)

FOREIGN PATENT DOCUMENTS

| | | |
|---|---|---|
| JP | 09-315882 A | 12/1997 |
| JP | 11-113843 | 4/1999 |

(Continued)

OTHER PUBLICATIONS

Japanese Office Action dated May 14, 2013 (and English translation thereof) in counterpart Japanese Application No. 2009-185760.

(Continued)

*Primary Examiner* — Matthew J Kasztejna
*Assistant Examiner* — Kevin G Barry, III
(74) *Attorney, Agent, or Firm* — Holtz, Holtz, Goodman & Chick PC

(57) ABSTRACT

The endoscope apparatus of the present invention includes: an insertion portion having a bending portion; an observation device that is provided at the insertion portion; an illumination unit that is provided at the insertion portion, and that illuminates a visual field of the observation device; a main body unit that is formed having a size that enables it to be held and operated by one hand of a user; an operating section that is used to operate the bending portion; a display unit that is connected to the insertion portion, and that displays images acquired by the observation device; a light emitting component that is provided in the main body unit, and that is connected via a light guide to the illumination unit; a heat discharge unit that is provided at the main body unit such that at least a portion thereof is exposed, and that is thermally connected to the light emitting component; and a shielding portion that is provided at the main body unit, and that covers at least a portion of the periphery of the heat discharge unit, and that also inhibits the heat discharge unit contacts with external portions thereof.

8 Claims, 15 Drawing Sheets

(56) References Cited

U.S. PATENT DOCUMENTS

| | | | |
|---|---|---|---|
| 5,879,289 A * | 3/1999 | Yarush et al. | 600/179 |
| 7,712,940 B2 | 5/2010 | Ogawa | |
| 2005/0129108 A1 | 6/2005 | Bendall et al. | |
| 2005/0168571 A1 | 8/2005 | Lia et al. | |
| 2006/0167340 A1* | 7/2006 | Pease et al. | 600/127 |
| 2006/0167531 A1* | 7/2006 | Gertner et al. | 607/86 |
| 2007/0129604 A1* | 6/2007 | Hatcher et al. | 600/136 |
| 2007/0187574 A1 | 8/2007 | Lia | |
| 2008/0009677 A1* | 1/2008 | Shoroji et al. | 600/160 |
| 2008/0116093 A1 | 5/2008 | Felten et al. | |
| 2008/0151046 A1 | 6/2008 | Scott et al. | |
| 2008/0152210 A1 | 6/2008 | Bendall | |
| 2008/0158348 A1 | 7/2008 | Karpen et al. | |
| 2009/0109045 A1 | 4/2009 | Delmonico et al. | |
| 2009/0109283 A1 | 4/2009 | Scott et al. | |
| 2009/0109429 A1* | 4/2009 | Scott et al. | 356/237.1 |
| 2009/0109431 A1 | 4/2009 | Delmonico et al. | |

FOREIGN PATENT DOCUMENTS

| | | |
|---|---|---|
| JP | 2002-013853 A | 1/2002 |
| JP | 2008-011992 A | 1/2008 |
| JP | 2008-48946 A | 3/2008 |
| JP | 2009-118966 A | 6/2009 |
| WO | WO 2009/055137 A1 | 4/2009 |

OTHER PUBLICATIONS

Japanese Office Action dated Mar. 4, 2014 (and English translation thereof) in counterpart Japanese Application No. 2009-185760.

* cited by examiner

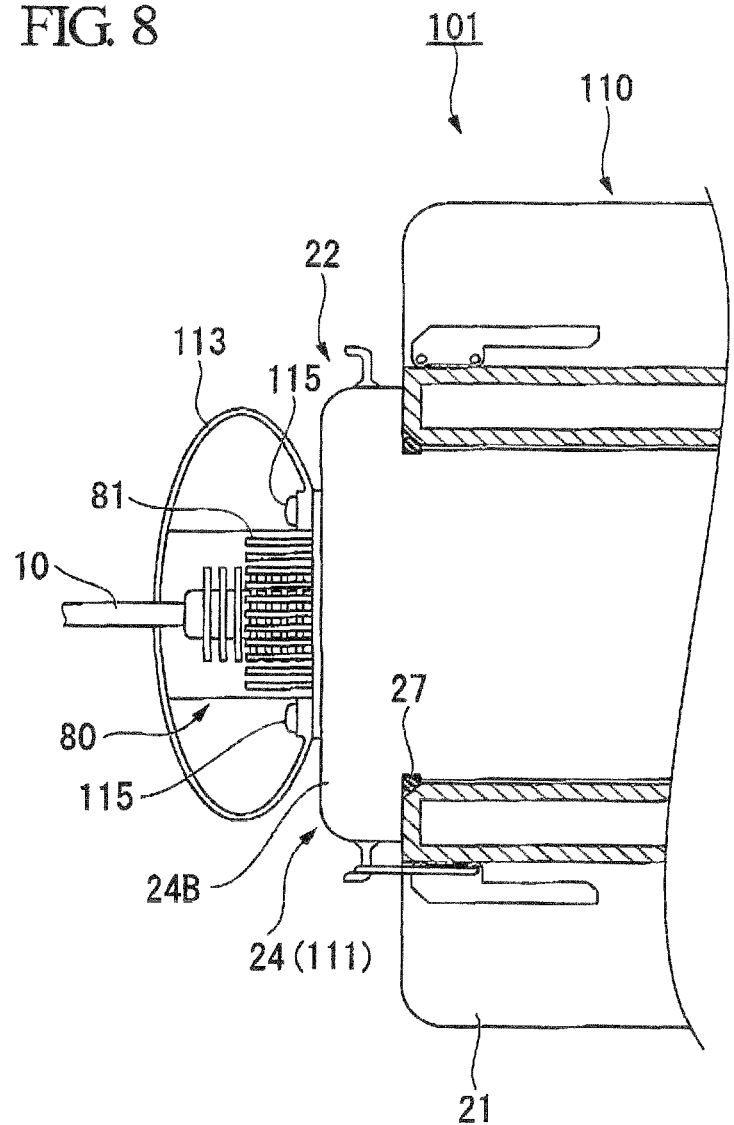

ENDOSCOPE APPARATUS

BACKGROUND OF THE INVENTION

1. Field of the Invention

The present invention relates to an endoscope apparatus that is used to observe internal portions of an examination subject. Priority is claimed on Japanese Patent Application No. 2009-185760, filed Aug. 10, 2009, the contents of which are incorporated herein by reference.

2. Description of Related Art

An endoscope apparatus provided with a flexible, elongated insertion portion is widely used in order to observe internal portions of a variety of examination subjects (see, for example, Japanese Patent Application Laid-Open (JP-A) No. 2008-48946). In this type of endoscope apparatus, an imaging device formed by a CCD or the like is provided on a distal end of the insertion portion. Images acquired by this imaging device are transmitted through the insertion portion to a main unit where they undergo image processing and the like and are then displayed on the display portion of a display unit or the like.

In many cases, light does not reach as far as the internal portions of an examination subject. Because of this, in normal endoscope apparatuses an operation is performed in which the visual field of the imaging device is made brighter (i.e., is illuminated) using an illumination mechanism that includes a light emitting component such as a light emitting diode (LED) or the like. A method in which the visual field of the imaging device is directly illuminated by placing a light emitting component on the distal end portion of the insertion portion, in the same way as for the imaging device, is known as a method for illuminating using an illumination mechanism. Moreover, a method of illuminating the visual field of an imaging device is known in which a light emitting component is placed on the main unit, and illumination light is guided to the distal end of the insertion portion by a light guide that is connected to the light emitting component.

In recent years, in order to make endoscope apparatuses easier to use, devices have been proposed (see, for example, United States Patent Application Publication No. 2009/0109429) in which an operating section that operates the insertion portion and the above described display unit are integrated into a single unit, and that are sufficiently miniaturized that they can be held in one hand. In this type of endoscope apparatus, the operating section, display unit, and main body are united in a single casing. A user uses the endoscope by directly holding the casing.

SUMMARY OF THE INVENTION

The endoscope apparatus of the present invention includes: an insertion portion having a bending portion; an observation device that is provided at the insertion portion; an illumination unit that is provided at the insertion portion, and that illuminates a visual field of the observation device; a main body unit that is formed having a size that enables it to be held and operated by one hand of a user; an operating section that is used to operate the bending portion; a display unit that is connected to the insertion portion, and that displays images acquired by the observation device; a light emitting component that is provided in the main body unit, and that is connected via a light guide to the illumination unit; a heat discharge unit that is provided at the main body unit such that at least a portion thereof is exposed, and that is thermally connected to the light emitting component; and a shielding portion that is provided at the main body unit, and that covers at least a portion of the periphery of the heat discharge unit, and that also inhibits the heat discharge unit contacts with external portions thereof.

BRIEF DESCRIPTION OF THE DRAWINGS

FIG. 8 is a partial bottom view showing a partial cross section of the main body unit shown in FIG. 7A.

PREFERRED EMBODIMENTS

Figure 1:
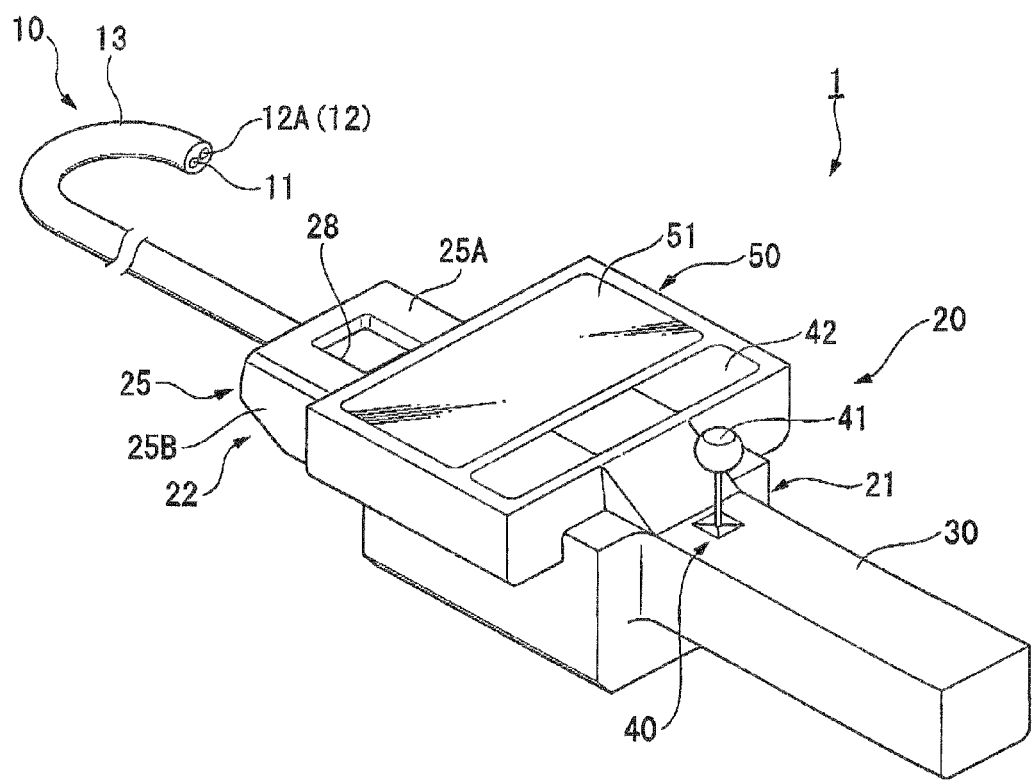
FIG. 1 is an overall perspective view showing an endoscope apparatus according to a first embodiment of the present invention.

A first embodiment of the present invention will now be described with reference made to FIG. 1 through FIG. 6B. FIG. 1 is an overall perspective view showing an endoscope apparatus 1 according to the present embodiment.

The endoscope apparatus 1 is provided with a flexible, elongated insertion portion 10, and a main body unit 20 that is connected to a proximal end of the insertion portion 10.

The insertion portion 10 is a portion that is inserted into the interior of an examination subject, and is formed as an elongated tubular component that has flexibility. The insertion portion 10 is provided with an imaging unit (i.e., an observation device) 11 and an illumination unit 12 that are provided at a distal end of the insertion portion 10, and with a bending portion 13 that is used to change the orientation of the distal end of the insertion portion 10 to a desired direction.

The imaging unit 11 has a known structure which is provided with an objective optical system (not shown) that forms images using reflection light from an observation location in the internal portion of the examination subject, and with an imaging element such as a CCD or the like that photoelectrically converts the reflection light from the observation location which has been formed into an image by the objective optical system. A signal wire (not shown) that is used for transmitting video signals acquired by the imaging element is connected to the imaging unit 11. This signal wire extends through the inside of the insertion portion 10 to the main body unit 20. If necessary, it is also possible for a known optical adapter that is used to adjust the angle of view, the direction of view, and the observation depth and the like of the imaging unit 11 to be mounted in the imaging unit 11.

The illumination unit 12 is constructed so as to contain an optical element or the like, and has an illumination light irradiation surface 12A at the distal end of the insertion portion 10, and illuminates the field of view of the imaging unit 11 using this illumination light. The light emitting component that is the light source of the illumination light is located inside the main body unit 20 and is described in detail below.

The bending portion 13 has a known structure which is formed by linking together in the direction of the center axis thereof a line of tubular node rings or bending links (referred to below as "node rings or the like"). The bending portion 13 is also able to perform a bending operation in a predetermined direction in which it moves away from the axis of the insertion portion 10. Transmission components (described below) such as wires or the like that are used to bend the bending portion 13 are inserted through each node ring or the like and are connected to the node ring or the like at the distal end side. In the endoscope system 1 of the present embodiment, the bending portion 13 is able to bend in four directions in which it moves away from the axis of the insertion portion 10. Four transmitting components which correspond to the respective directions pass through the interior of the insertion portion 10 and extend as far as the main body unit 20.

The main body unit 20 is provided with a casing portion 21 which is held by a user when the user performs an operation, and with a drive unit 22 that is removably mounted on the casing portion 21, and that generates motive power to drive the bending portion 13 of the insertion portion 10.

The casing portion 21 is provided with a holding portion 30 which is held by a user, an operating section 40 that is used to perform operating input for the bending portion 13, and a display unit 50 that displays video signals acquired by the imaging unit 11 as images.

Figures 2A, 2B:
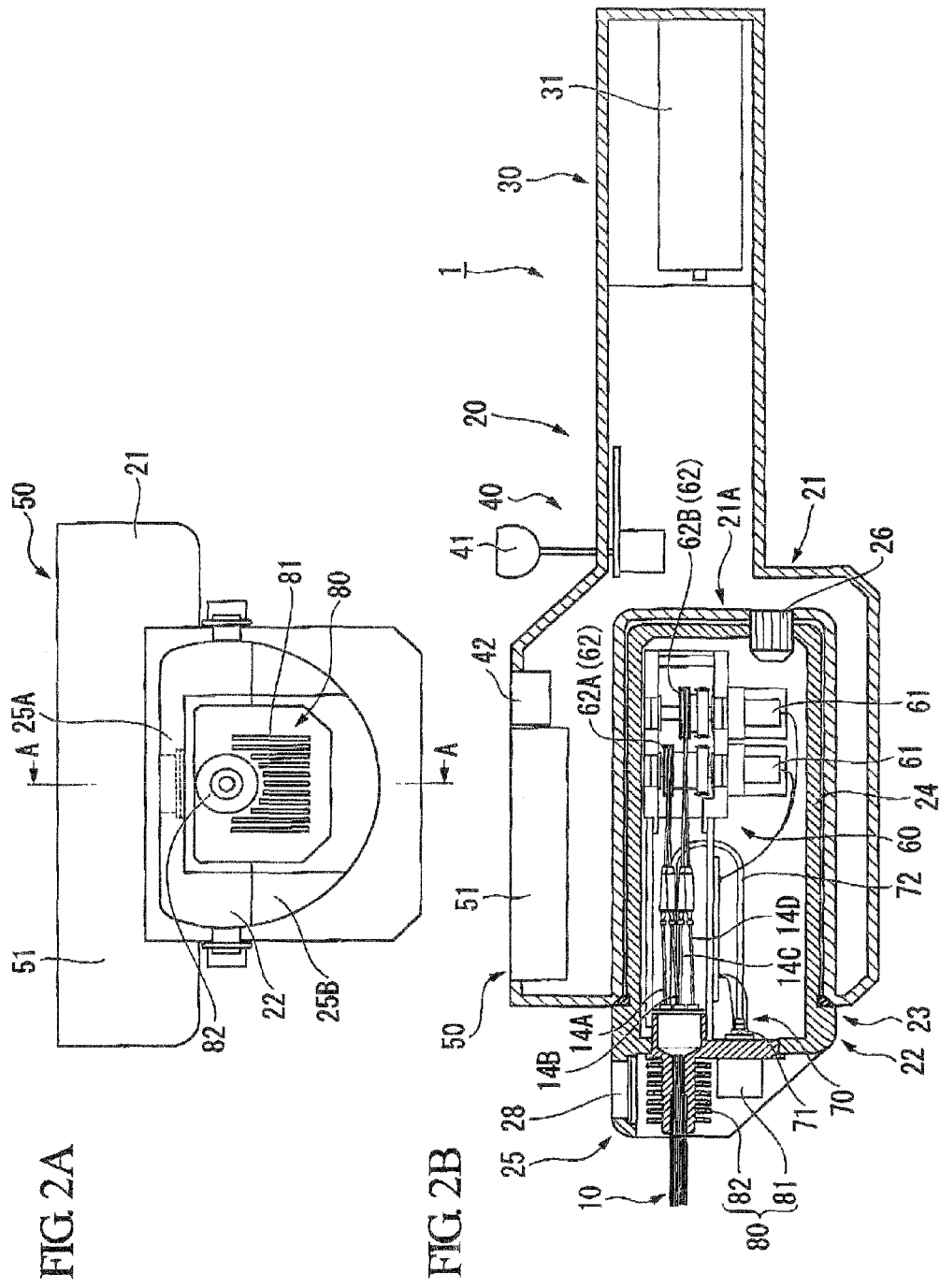
FIG. 2A is a front view of a main body unit of the endoscope apparatus according to FIG. 1.
FIG. 2B is a cross-sectional view taken along a line A-A in FIG. 2A.

FIG. 2A is a front view of the main body unit 20, while FIG. 2B is a cross-sectional view taken along a line A-A in FIG. 2A. The holding portion 30 is formed in a rod shape having a size that enables it to be held in one hand by a user, and a battery 31 that forms a power supply for the drive unit 22 and the display unit 50 is housed inside the holding portion 30.

The operating section 40 is provided with a joystick 41 that can be operated in four directions, and with a plurality of buttons 42, and can be used for inputting the operating direction of the bending portion 13 and for inputting various settings and the like for the display unit 50. Instead of the joystick 41, it is also possible to employ keys or buttons or the like that correspond to the four operating directions.

The display unit 50 is provided with a display screen 51, and with an image processing section (described below) that processes video signals transmitted from the imaging unit 11 such that they can be displayed on the display screen 51. Various types of known mechanisms can be appropriately selected and employed for the display screen 51 and the image processing section. It is also possible for what is known as a touch panel type of display which has the functions of the buttons 42 of the operating section 40 to be employed for the display screen 51.

The drive unit 22 is provided with outer packaging 23 that is removably mounted on the casing portion 21, a drive mechanism 60 and a light source section 70 that are housed inside the outer packaging 23, and a heat discharge unit 80 that is thermally connected to the light source section 70.

The drive mechanism 60 is provided with two groups that are each made up of a drive source in the form of a motor 61, and a pulley 62 that is rotated by the motor 61. There is no particular limitation on the method used to link together the motor 61 and pulley 62, and it is sufficient for the pulley 62 to be attached to a shaft of the motor 61. It is also possible for the shaft and the rotation shaft of the pulley 62 to be connected by means of a power transmission component such as a belt or the like.

Of the four angle wires that are connected as transmission components to the bending portion 13, two angle wires 14A and 14B that cause the bending portion 13 to bend in two directions which are parallel to the A-A line shown in FIG. 2A and which also move away from the axis of the insertion portion 10 (hereinafter referred to as "up-down directions") are connected to one pulley 62A. In addition, two angle wires 14C and 14D that cause the bending portion 13 to bend in two directions which are orthogonal to the up-down directions and which also move away from the axis of the insertion portion 10 (hereinafter referred to as "left-right directions") are connected to another pulley 62B.

By employing the above described structure, when the two motors 61 are rotated, the corresponding pulleys 62A and 62B are also rotated, and the pair made up by the angle wires 14A and 14B and the pair made up by the angle wires 14C and 14D are moved by a desired amount relatively to the insertion portion 10. As a result of this, in the present embodiment, the bending portion 13 can be made to bend in a desired direction.

The light source section 70 is provided with a light emitting element which forms a light emitting component, for example, an LED (Light Emitting Diode) 71 that emits illumination light, and a light guide 72 that is connected to the LED 71. The light guide 72 exits to the outside of the outer packaging 23 and then enters the interior of the insertion portion 10 which is connected to the outer packaging 23. It then passes through the interior of the insertion portion 10, and is connected to the illumination unit 12.

The heat discharge unit 80 is formed from a material having superior thermal conductivity such as metal or the like, and it is attached to a connection portion between the outer packaging 23 and the insertion portion 10. A portion of the heat discharge unit 80 is inserted inside the outer packaging 23 and is thermally connected to the LED 71. The heat discharge unit 80 has a plurality of first fins 81 that extend in the axial direction of the insertion portion 10, and a plurality of disk-shaped second fins 82 that extend in the radial direction of the insertion portion 10. The heat discharge unit 80 employs the first fins 81 and the second fins 82 that are exposed to the outside of the main body unit 20 so as to function as a heat sink that allows the heat generated by the LED 71 to escape to the outside of the main body unit 20.

Figure 3:
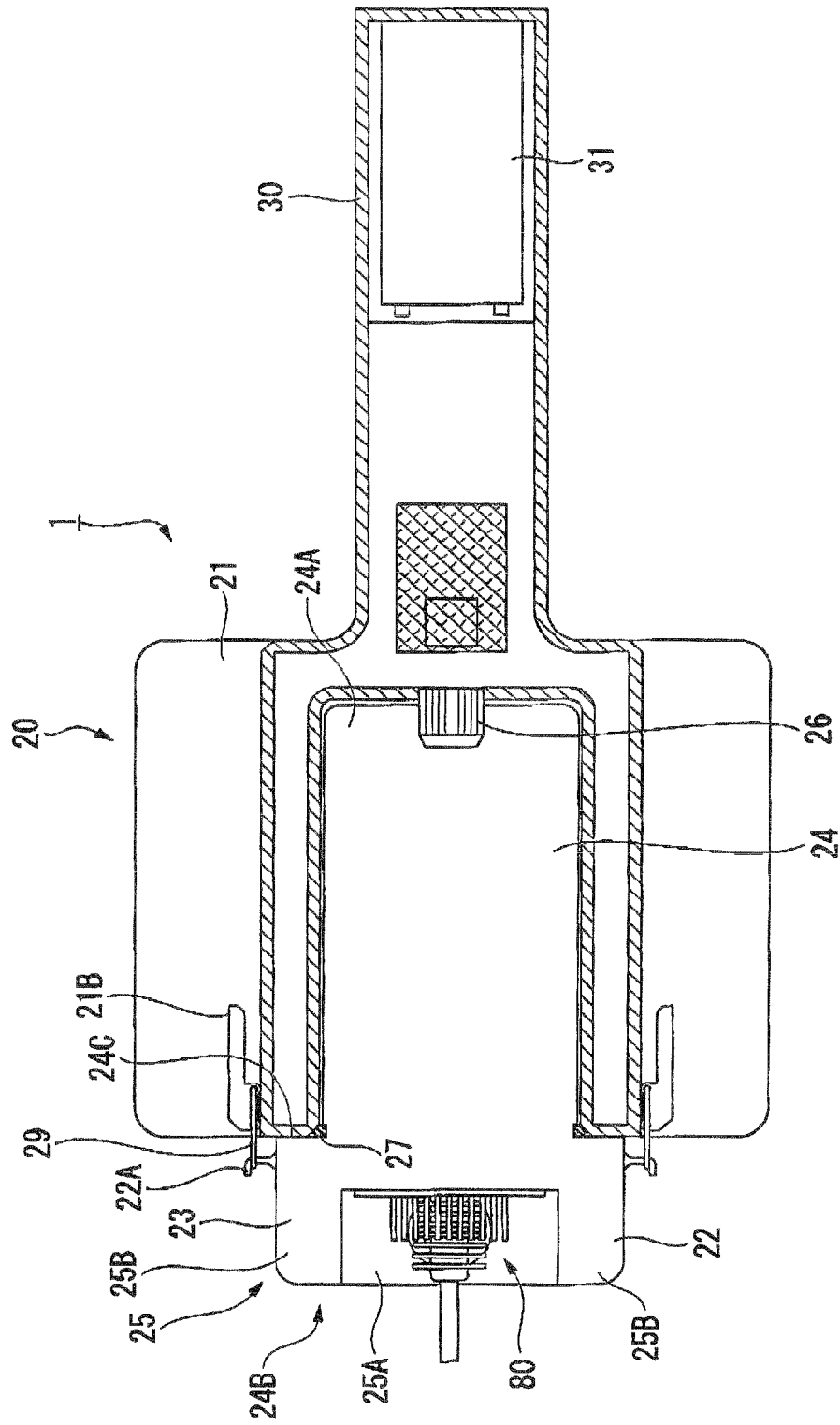
FIG. 3 is a partial cross-sectional view showing the main body unit of FIG. 2A as seen from underneath.

FIG. 3 is a partial cross-sectional view showing a state in which the main body unit 20 is seen from below (i.e., from the opposite side to the side where the display unit 50 is provided). The outer packaging 23 is formed from resin or the like and, as is shown in FIG. 2B and FIG. 3, is provided with a housing portion 24 that internally houses the drive mechanism 60, the LED 71 and the like, and with a shielding portion 25 that is connected to the housing portion 24 and covers the periphery of the heat discharge unit 80 so as to restrict external contact therewith.

The housing portion 24 is formed substantially in a box shape. A connector 26 that is used for connecting to the casing portion 21 is provided on a first end portion 24A of the housing portion 24. In contrast, as is shown in FIG. 3, a second end portion 24B which is located on the opposite side from the first end portion 24A is formed having larger dimensions in the up-down and left-right directions than the first end portion 24A. In addition, a step portion 24C is formed in a portion where these dimensions change. An annular sealing component 27 which is formed from an elastically deformable material is mounted around the entire circumference of the step portion 24C.

The shielding portion 25 is formed so as to extend from the second end portion 24B of the housing portion 24 towards the distal end side of the insertion portion 10. In addition, the shielding portion 25 has a top plate portion 25A that extends above the heat discharge unit 80, and side wall portions 25B that extend in two locations on the left and right of the heat discharge unit 80. As is shown in FIG. 3, the shielding portion 25 is not provided below the heat discharge unit 80.

There are no particular restrictions on the dimensions of the top plate portion 25A and side plate portions 25B. However, as is described below, it is preferable for these dimensions to be set such that the top and sides of the heat discharge unit 80 are completely covered so that a user does not unintentionally touch the heat discharge unit 80.

A through hole 28 is provided in the top plate portion 25A. Because the bottom of the heat discharge unit 80 is not covered by the shielding portion 25, air surrounding the heat discharge unit 80 is able to circulate in top and bottom directions through the through hole 28. Namely, the circulation of air around the heat discharge unit 80 is promoted by the through hole.

There are no particular restrictions on the dimensions of the through hole 28, however, a large size is preferable from the standpoint of good air circulation, while dimensions that do not permit a typical person to insert their finger therein are preferable from the standpoint of inhibiting a user from touching the heat discharge unit 80. Accordingly, the shape is preferably set such that a typical person cannot insert a finger therein, while being set to as large a size as possible.

As is shown in FIG. 2B and FIG. 3, the one end portion 24A of the drive unit 22 is inserted into a receptacle portion 21A which is a space provided beneath the display unit 50 in the casing portion 21. In addition, as a result of the connector 26 been connected with a receptor (not shown) which is provided in the receptacle portion 21A, the casing portion 21 and the drive unit 22 are removably connected together so as to form the integrated main body unit 20. At this time, as is shown in FIG. 3, hooks 21B and 22A that are provided respectively in the casing portion 21 and drive unit 22 may be linked together by means of a linking component 29, so that the drive unit 22 can be prevented from becoming accidentally dropped out from the casing portion 21.

The main body unit 20 of the endoscope apparatus 1 which is formed by uniting the casing portion 21 and drive unit 22 in a single body has a size and weight that enable it to be held in one hand when a user is holding the holding portion 30. In addition, in the endoscope apparatus 1, the joystick 41 and buttons 42 of the operating section 40 are able to be operated while the holding portion 30 is being held by a user.

Figure 4:
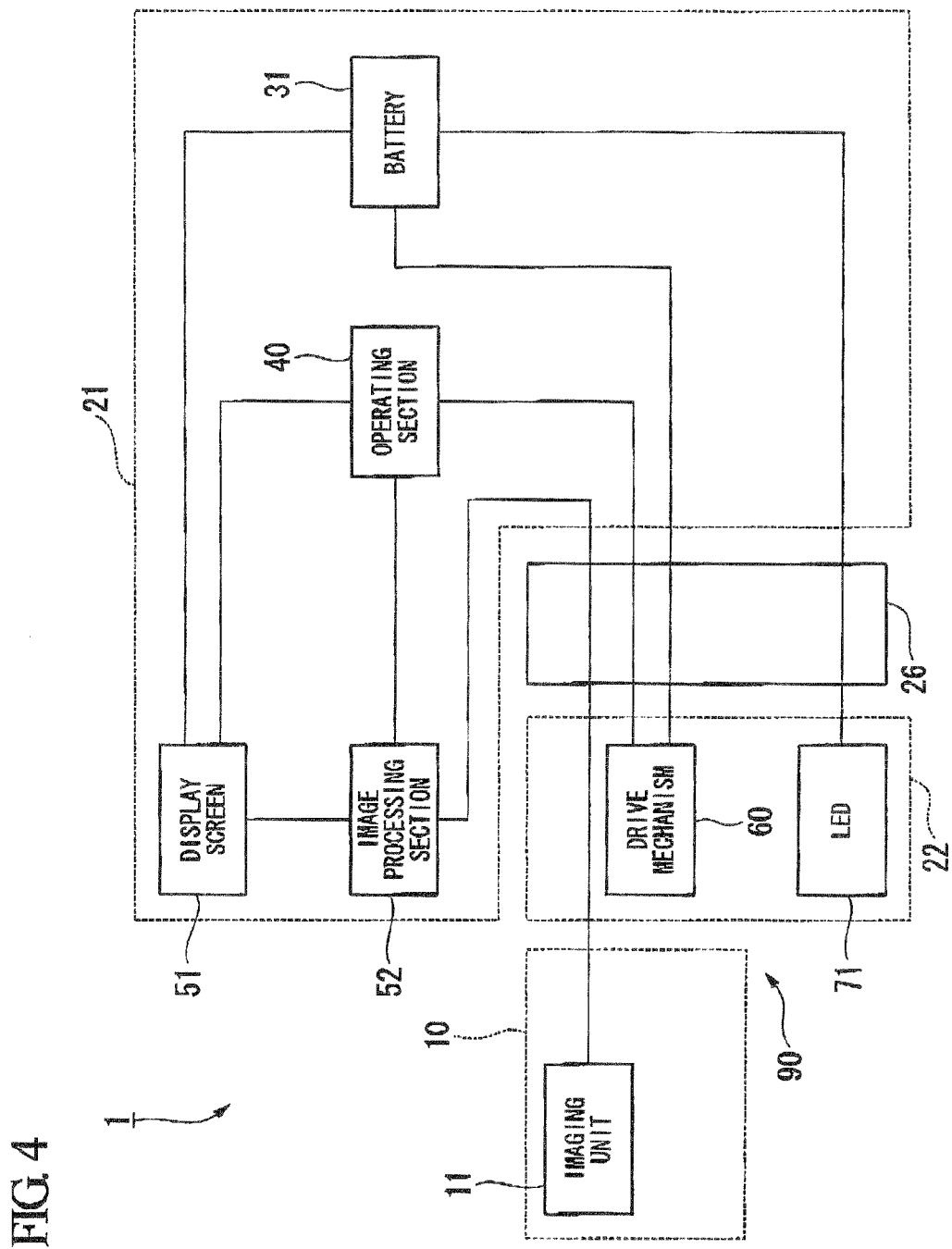
FIG. 4 is a block diagram showing connections between each section of the endoscope apparatus according to FIG. 1.
Figure 5A:
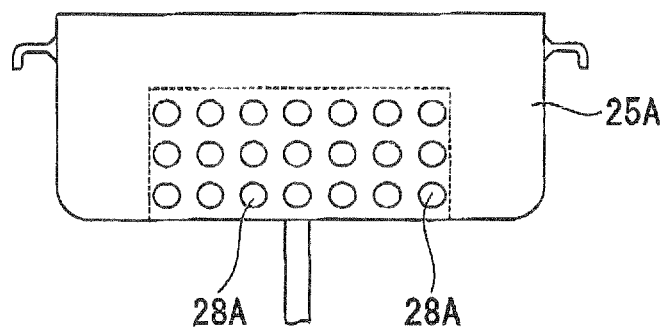
FIG. 5A is a view showing an embodiment of a top plate portion of a shielding portion according to the first embodiment of the present invention.
Figure 5B:
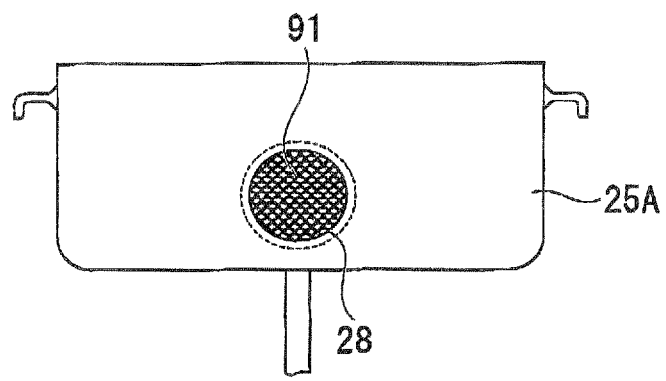
FIG. 5B is a view showing another embodiment of a top plate portion of a shielding portion according to the first embodiment of the present invention.

FIG. 4 is a block diagram showing electrical connections between each section of the endoscope apparatus 1. In the casing portion 21, the operating section 40 is connected to the display screen 51 and to an image processing section 52 of the display unit 50.

The battery 31 is connected to the display screen 51.

When the casing portion 21 and drive unit 22 are connected via the connector 26, the battery 31 and the drive mechanism 60 and LED 71 are connected together and power is supplied to these mechanisms. At the same time, the imaging unit 11 of the insertion portion 10 and the image processing section 52 are connected together, and the drive mechanism 60 and the operating section 40 are connected together.

In the present embodiment, the drive unit 22 and the insertion portion 10 which is connected to the drive unit 22 are formed as an integrated insertion portion unit 90. Because of this, it is possible to switch between a plurality of insertion portion units in which the settings of the imaging unit 11 or the lengths of the insertion portion 10 are different so as to match the type of examination subject or the purpose of use of the endoscope apparatus 1.

An operation when the endoscope apparatus 1 having the above described structure is in use will now be described.

Firstly, a user selects one insertion portion unit 90 and inserts the first end portion 24A of the drive unit 22 into the receptacle portion 21A so as to connect together the connector 26 and the receptor. At this time, the sealing component 27 that is mounted on the step portion 24C of the housing portion 24 closes off the gap between the housing portion 24 and the receptacle portion 21A, so that the casing portion 21 and the drive unit 22 are connected together in a watertight state. After making this connection, the user starts up the endoscope apparatus 1.

The user then inserts the insertion portion 10 into the interior of an examination subject. The visual field of the imaging unit 11 is illuminated by the illumination unit 12, and video signals acquired by the imaging unit 11 are processed by the image processing section 52. Images of the interior of the examination subject are then displayed on the display screen 51.

The user then moves the distal end of the insertion portion 10 towards an observation target while changing the orientation of the distal end of the insertion portion 10 by operating the operating section 40 as is required, while at the same time verifying the images displayed on the display screen 51. When the distal end of the insertion portion 10 has reached the observation target, the user causes the bending portion 13 to bend in a desired direction, and observes the observation target.

As the usage time of the endoscope apparatus 1 lengthens, the temperature of the LED 71 of the light source section 70 increases.

The heat generated from the LED 71 is transmitted to the heat discharge unit 80 which is thermally connected to the LED 71, and is dispersed to the outside of the main body unit 20 from the first fins 81 and the second fins 82. The air surrounding the heat discharge unit 80 is suitably dispersed from the through hole 28 provided in the shielding portion 25 and from the bottom of the heat discharge unit 80 which is not covered by the shielding portion 25. As a result of this, any harmful effects of heat on the respective mechanisms housed in the housing portion 24 are inhibited.

When the insertion portion unit 90 is replaced with another unit, the insertion portion 10 is extracted from the examination subject, and the power supply of the endoscope apparatus 1 is turned off. In addition, while holding the holding portion 30 with one hand, the user holds the base end side of the insertion portion 10 or the vicinity of the second end portion 24B of the drive unit 22 with the other hand, and extracts the drive unit 22 from the casing portion 21.

When the light emitting component such as the LED 71 or the like is located inside the main body unit 20, as is the case with the endoscope apparatus 1, it is common for the heat discharge unit 80 to stay at a high temperature for a short time after the power supply has been turned off. Because of this, it is necessary for the user to pay careful attention during the above described operation to extract the drive unit 22. In the endoscope apparatus 1 of the present embodiment, the shielding portion 25 covers the top and sides of the heat discharge unit 80, while the dimensions and the like of the through hole 28 are set such that a typical person is unable to insert their finger therein. Because of this, any possibility of the user touching the heat discharge unit 80 which is still hot is suitably inhibited during the operation to extract the drive unit 22 or when the endoscope apparatus 1 is being carried or the like.

According to the endoscope apparatus 1 of the present embodiment, at least a portion of the area surrounding the heat discharge unit 80 which becomes extremely hot when the heat from the LED 71 is transmitted thereto during use and after use is covered by the shielding portion 25. As a result of this, the heat discharge unit 80 is suitably inhibited from coming into contact with any portion of the user's body. Accordingly, it is not necessary for the user to pay special attention to the heat discharge unit 80 during use, and the endoscope apparatus is easy to use while being able to be held with one hand.

Moreover, because the through hole 28 is provided in the top plate portion 25A of the shielding portion 25, the air surrounding the heat discharge unit 80 is properly circulated in the up-down directions. Accordingly, the heat of the heat discharge unit 80 is properly dispersed, and the heat of the LED 71 can be allowed to escape efficiently to the outside.

In the present embodiment, an example is described in which a single through hole 28 is provided in the top plate portion 25A. However, as in the variant example shown in FIG. 5A, it is also possible to form a plurality of narrow-diameter through holes 28A in the top plate portion 25A. Moreover, as in the variant example shown in FIG. 5B, it is also possible to mount a mesh component 91 which allows air to circulate in the through hole 28. These structures also enable the circulation of air around the heat discharge unit 80 to be promoted while, inhibiting any contact by a user with the heat discharge unit 80. Instead of using the mesh component, it is also possible to form a rib spanning across the through hole. Note that it is also possible to provide the mesh component or rib below the heat discharge unit 80, so that any contact by a user with the heat discharge unit 80 is even more reliably inhibited.

Moreover, instead of providing a through hole in the top plate portion 25A, it is also possible to allow air to circulate around the heat discharge unit 80 by providing through holes in the two side wall portions 25B. However, if the fact that air warmed by the heat discharge unit 80 tends to rise upwards, and the fact that it is easy for a user to hold the side wall portions 25B during the operation to extract the drive unit 22 are considered, then it is more preferable for the through hole to be provided in the top plate portion 25A.

Figure 6A:
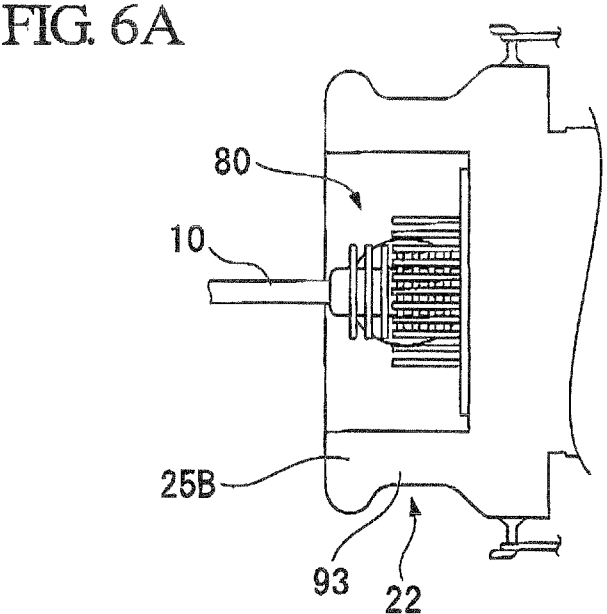
FIG. 6A is a view showing an embodiment of a side wall portion of a shielding portion according to the first embodiment of the present invention.
Figure 6B:
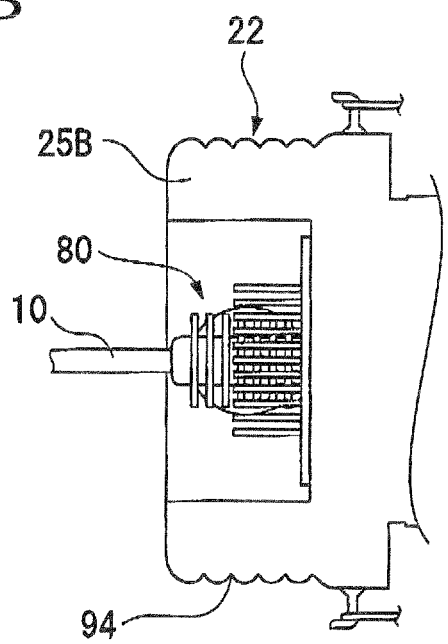
FIG. 6B is a view showing another embodiment of a side wall portion of a shielding portion according to the first embodiment of the present invention.

Furthermore, as is shown in FIG. 6A and FIG. 6B, it is also possible for a recessed portion 93 or rib portions 94 to be formed as removal holding portions in the side wall portions 25B in order to make the operation to extract the drive unit 22 easier to perform.

Figure 9:
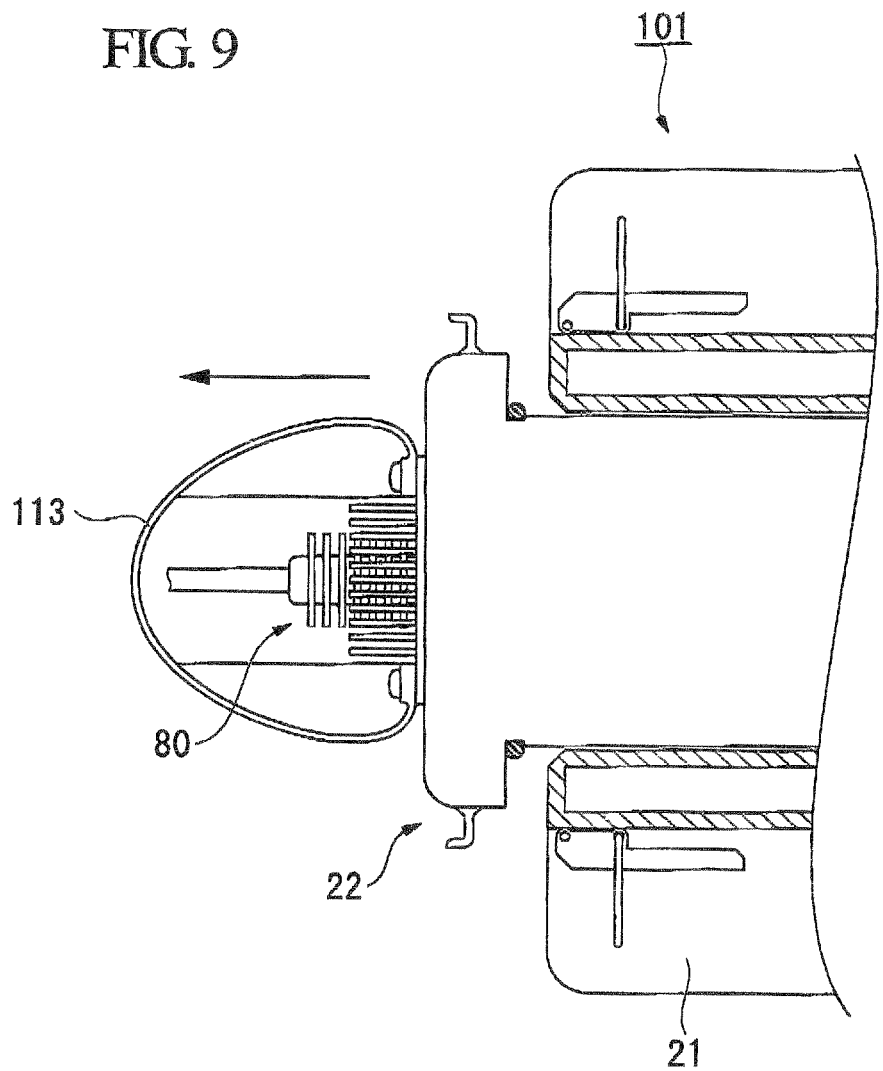
FIG. 9 is a view showing an operation when the endoscope apparatus according to the second embodiment of the present invention is in use.

Next, a second embodiment of the present invention will be described with reference made to FIG. 7 through FIG. 9. The structure of an endoscope apparatus 101 of the present embodiment differs from that of the endoscope apparatus 1 of the above described first embodiment in the shape of the shielding portion. Note that, in the following descriptions of the respective embodiments, structure which is common to previously described embodiments is given the same symbol and any duplicate description thereof is omitted.

Figure 7A:
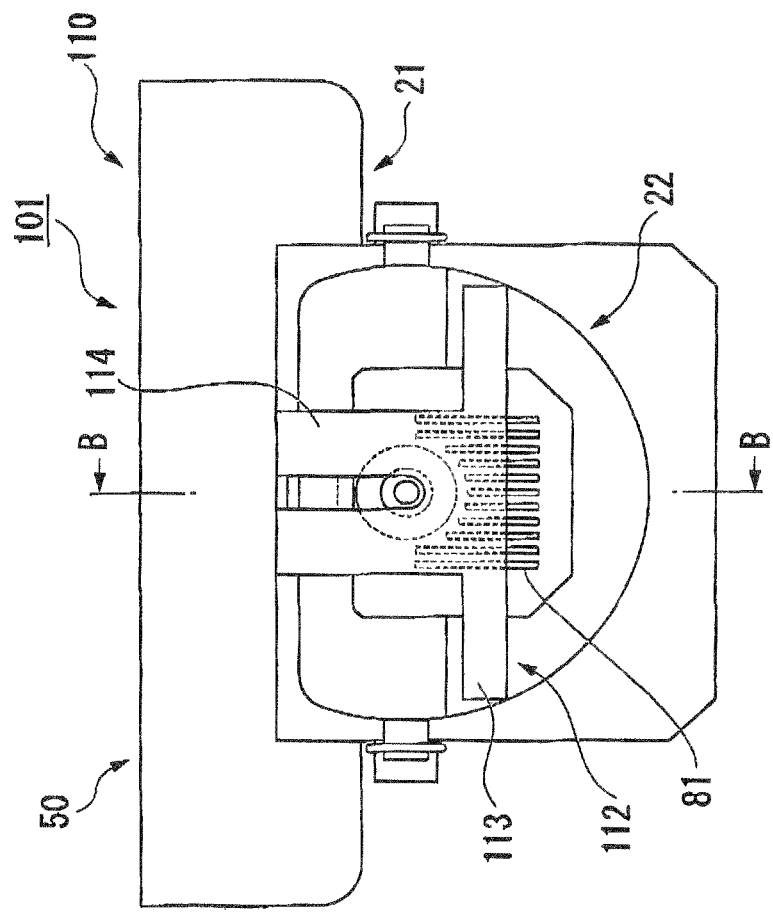
FIG. 7A is a front view of a main body unit of an endoscope apparatus according to a second embodiment of the present invention.
Figure 7B:
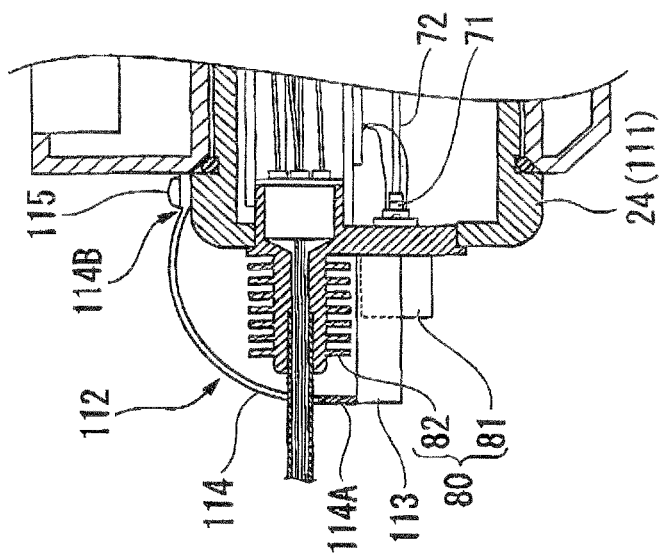
FIG. 7B is a partial cross-sectional view taken along a line B-B in FIG. 7A.

FIG. 7A is a front view of a main body unit 110 of the endoscope apparatus 101, while FIG. 7B is a partial cross-sectional view taken along a line B-B in FIG. 7A. A shielding portion 112 is provided instead of the shielding portion 25 in an outer packaging 111 of the drive unit 22.

The shielding portion 112 is provided with a first component 113 and a second component 114 which are flexible and belt-shaped. The first component 113 is formed from resin or the like. As is shown in FIG. 8, the first component 113 is positioned such that the transverse direction thereof is parallel with the up-down direction of the bending portion 13, and so as to form a ring shape surrounding and covering the sides and front of the first fins 81 of the heat discharge unit 80. The two ends in the longitudinal direction of the first component 113 are fixed to the second end portion 24B of the housing portion 24 by means of screws 115 or the like.

The second component 114 is formed from the same type of material as the first component 113, and a first end portion 114A thereof is connected to the first component 113 on the insertion portion 10 side than the heat discharge unit 80. The second component 114 extends towards the outer packaging 111 so as to cover the top of the heat discharge unit 80. A second end portion 114B is fixed to the second end portion 24B of the housing portion 24 by means of screws 115 or the like.

A slit 114C that is intended to prevent interference with the insertion portion 10 is formed in the second component 114. The slit 114C extends as far as the second end portion 114B, and the second end portion 114B is divided into two forks. The configuration that prevents any interference with the insertion portion 10 is not restricted to the configuration described above, and it is sufficient for the first end portion 114A side to be divided into two forks by the slit 114C. Moreover, it is also possible for a hole or elongated hole or the like that does not divide the end portion into two forks to be formed in the second component 114. Furthermore, it is also possible for two individual components to be provided such that they sandwich the insertion portion 10 from the left and right sides. It is also possible for the first component 113 to have a configuration such as a slit that prevents interference.

In the endoscope apparatus 101 having the above described structure, a portion of the body of a user such as the fingers or the like that approach the heat discharge unit 80 from the sides or top thereof firstly come into contact easily with the first component 113 and the second component 114 of the shielding component 112. Accordingly, it is possible to suitably inhibit a user coming into contact with the heat discharge unit 80 which has become extremely hot while the endoscope apparatus 101 has been in use.

When the drive unit 22 is removed from the casing portion 21, the user places their fingers on the first component 113, and pulls the drive unit 22 such that it moves away from the casing portion 21. As a result, as is shown in FIG. 9, the belt-shaped first component 113 is deformed towards the distal end side of the insertion portion 10. Because of this, the fingers or the like that had been placed on the first component 113 are kept at a distance from the heat discharge unit 80 and do not accidentally touch the heat discharge unit 80.

In the endoscope apparatus 101 of the present embodiment as well, the heat discharge unit 80 is suitably inhibited from coming into contact with any portion of the user's body, and the endoscope apparatus is made easy to use.

In addition, the shielding portion 112 is formed by the belt-shaped first component 113 and second component 114. Because of this, in the endoscope apparatus 101 of the present embodiment, the shielding portion 112 can be used as a handle when the drive unit 22 is being removed from the casing portion 21. Consequently, in the endoscope apparatus 101 of the present embodiment, the outer packaging of the drive unit can be reduced in size, and the ease of use of the main body unit 110 can be further improved.

In the present embodiment, the respective dimensions such as the width and length of the first component 113 and second component 114 can be suitably set. For example, as is shown in FIG. 8, it is preferable for the length to be set such that a suitable gap is left between the first component 113 and the heat discharge unit 80, as this makes it difficult for a finger or the like to touch the heat discharge unit 80 when a finger or the like is inserted inside the ring formed by the first component 113 in order to use it as a handle. Moreover, if the width dimension of the first component 113 is set to approximately the dimension in the up-down direction of the overall heat discharge unit 80 including the first fins 81 and the second fins 82, then it is possible to cover the sides of the entire heat discharge unit 80, and more favorably inhibit any contact with the heat discharge unit 80. Note that if the heat discharge unit 80 is excessively enclosed by the shielding portion 112, then the flow of air around the heat discharge unit 80 is adversely affected and the cooling efficiency deteriorates. Therefore, it is preferable for a suitable gap to be maintained between the shielding portion and the heat discharge unit.

Moreover, in the present embodiment, an example is described in which the shielding portion is made up of two different types of components, namely, a first component and a second component, however, instead of this it is also possible for the shielding portion to be formed only by either one of the first component or the second component.

Next, a third embodiment of the present invention will be described with reference made to FIG. 10 through FIG. 13. The structure of an endoscope apparatus 121 of the present embodiment differs from the structures of the endoscope apparatuses of the above described respective embodiments in the configuration of the heat discharge unit and shielding portion.

Figure 10:
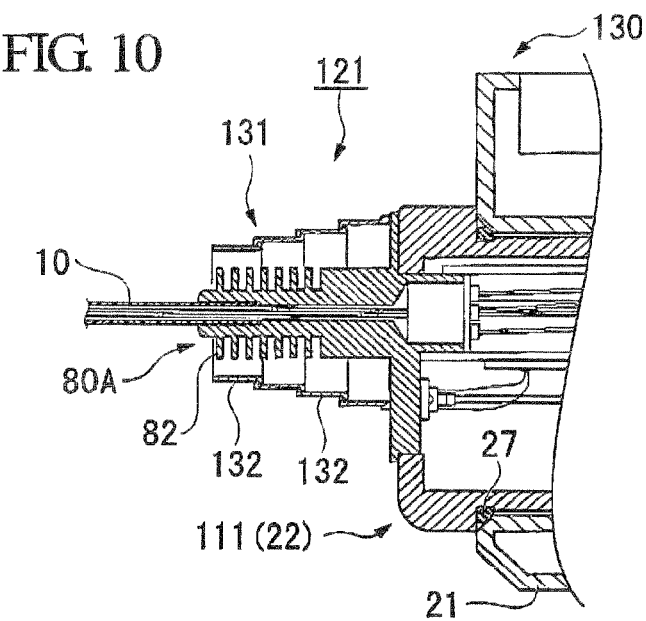
FIG. 10 is a partial cross-sectional view as seen from a side showing a main body unit of an endoscope apparatus according to a third embodiment of the present invention.
Figure 11:
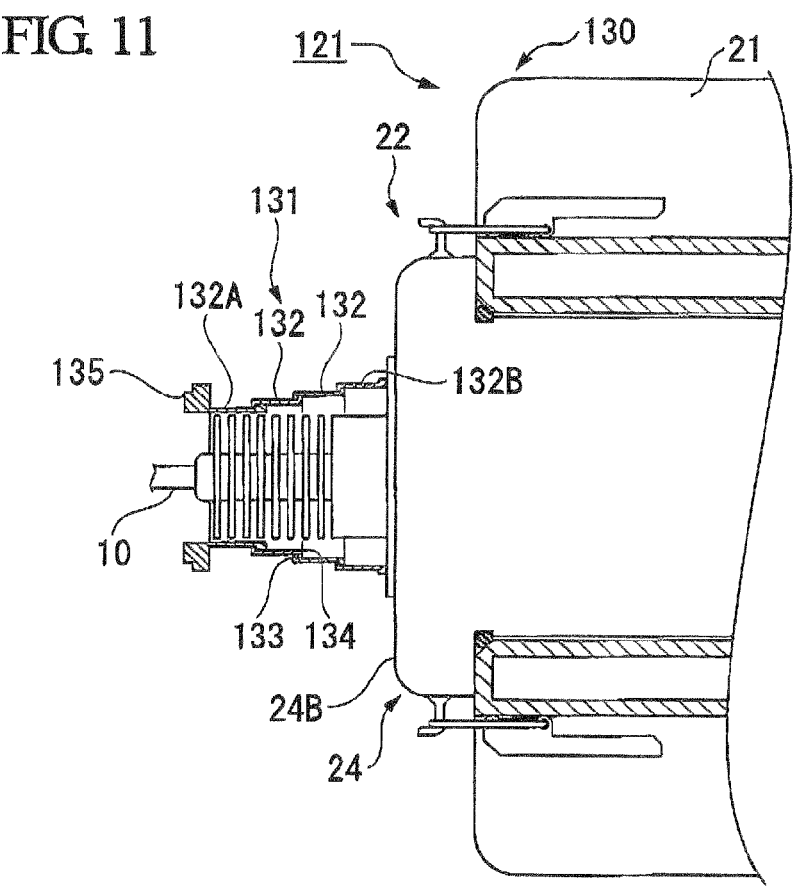
FIG. 11 is a partial bottom view showing a partial cross section of the main body unit shown in FIG. 10.

FIG. 10 is a partial cross-sectional view as seen from a side showing a main body unit 130 of the endoscope apparatus 121, while FIG. 11 is a partial bottom view showing a partial cross-section of the main body unit 130. As is shown in FIG. 10 and FIG. 11, instead of the shielding portion 25, a shielding portion 131 is provided on the outer packaging 111 of the drive unit 22. A heat discharge unit 80A does not have the first fins 81, and is only provided with the circular disk-shaped second fins 82.

The shielding portion 131 has a known telescopic structure in which a plurality of tubular components 132 which each have a different diameter are arranged substantially coaxially so as to be able to move relatively in the axial direction. The plurality of tubular component 132 are lined up such that their diameters become larger moving from the distal end side of the insertion portion 10 towards the main body unit 130. Engaging portions 133 that protrude on the inner side in the radial direction are provided at the distal end side of each tubular component 132. As a result of each engaging portion 133 engaging with flanges 134 that protrude on the outer side in the radial direction at the base end side of the tubular component positioned on the distal end side of itself, the respective tubular components are linked together such that they do not become dropped out from each other. As is shown in FIG. 11, a dial 135 that protrudes on the outer side in the radial direction is provided on a tubular component 132A located furthest on the distal end side. A tubular component 132B located furthest on the base end side is fixed to the second end portion 24B of the housing portion 24.

Figure 12:
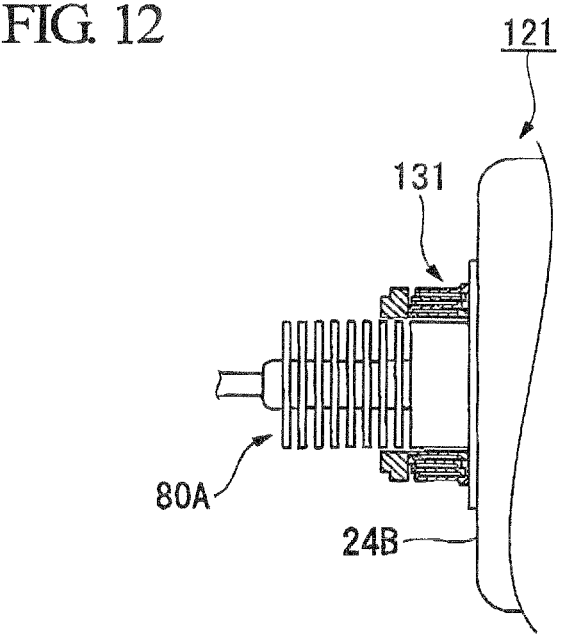
FIG. 12 is a view showing a state in which the shielding portion of the endoscope apparatus according to the third embodiment of the present invention is folded.
Figure 13:
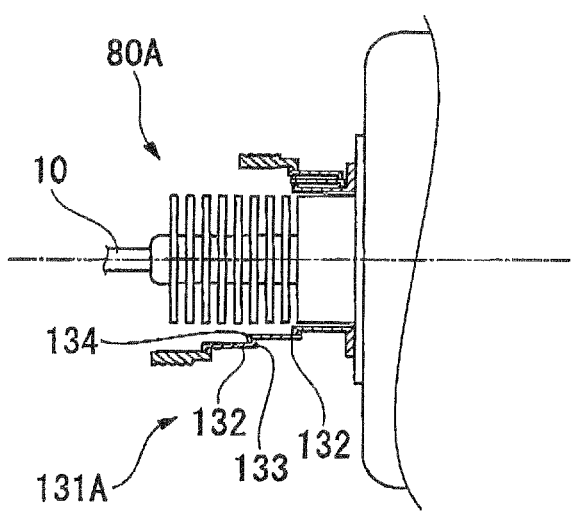
FIG. 13 is a view showing another embodiment of the shielding portion according to the third embodiment of the present invention.

As is shown in FIG. 12, when the endoscope apparatus 121 is in use, the shielding portion 131 is folded on to the second end portion 24B side so that the heat discharge unit 80A is exposed, and heat from the heat discharge unit 80A can be efficiently dispersed to the outside. Because it is uncommon for a user to bring their hand or the like close to the heat discharge unit 80A when the endoscope apparatus 121 is in use, no serious problems arise.

When removing the drive unit 22 from the casing portion 21, the user holds the dial 135 and pulls it towards the distal end side of the insertion portion 10. Consequently, as is shown in FIG. 10 and FIG. 11, the respective tubular components 132 of the shielding portion 131 are moved towards the distal end side of the insertion portion 10 until the engaging portions 133 come up against the flanges 134. As a result of this, the shielding portion 131 extends towards the distal end side of the insertion portion 10 and covers the periphery of the heat discharge unit 80A. In this manner, on occasions such as when the drive unit 22 is being switched and it is easy for the fingers or the like of a user to come into contact with the heat discharge unit 80A, the user is suitably inhibited from coming into contact with the heat discharge unit 80A.

In the endoscope apparatus 121 of the present embodiment as well, the heat discharge unit 80 is suitably inhibited from coming into contact with any portion of the user's body, and the endoscope apparatus is made easy to use.

Moreover, when the shielding portion 131 is pulled towards the distal end side of the insertion portion 10, the entire periphery of the heat discharge unit 80A can be covered. Because of this, is possible to more reliably inhibit a portion of the body of a user coming into contact with the comparatively high-temperature heat discharge unit 80A. On the other hand, if the shielding portion 131 is folded, then the periphery of the heat discharge unit 80A becomes substantially completely exposed. As a result, heat from the heat discharge unit 80A can be efficiently dispersed to the outside when the endoscope apparatus 121 is in use.

In this manner, the shielding portion 131 is able to change its shape and switch between a state in which the periphery of the heat discharge unit 80A is covered, and a state in which the heat discharge unit 80A is uncovered and is instead exposed. Accordingly depending on the situation, the shielding portion 131 can be changed to a suitable shape and is made easy to use.

In the present embodiment, an example is described in which the plurality of tubular components 132 of the shielding portion 131 are arranged in a sequence in which the diameter becomes larger moving inwards from the distal end side of the insertion portion 10. However, as in the variant example shown in FIG. 13, it is also possible to form a shielding portion 131A in which the plurality of tubular components 132 are arranged in a sequence in which the diameter becomes smaller moving inwards from the distal end side of the insertion portion 10. In this case, the engaging portions 133 are provided on the base end side of each tubular component, and each one engages with the flange 134 that is provided on the distal end side of the adjacent tubular component. Note that in FIG. 13, the top half of the shielding portion 131A is shown in a state in which the shielding portion 131A is folded.

If the shielding portion 131A is formed having the above described structure, then when the periphery of the heat discharge unit 80A is covered by the shielding portion 131A, a larger gap is maintained on the distal end side between the shielding portion 131A and the heat discharge portion 80A. Accordingly, there is an improved airflow around the heat discharge unit 80A, and it is possible to inhibit any deterioration in the cooling efficiency of the heat discharge unit 80A even when the periphery of the heat discharge unit 80A is covered by the shielding portion 131A. Moreover, because the tubular component located furthest on the distal end side which is touched during the extraction operation is furthest from the heat discharge unit 80A, the extraction operation is further simplified.

Next, a fourth embodiment of the present invention will be described with reference made to FIG. 14 through FIG. 17. The structure of an endoscope apparatus 141 of the present embodiment differs from the structures of the endoscope apparatuses of the above described respective embodiments in the configuration of the shielding portion.

Figure 14:
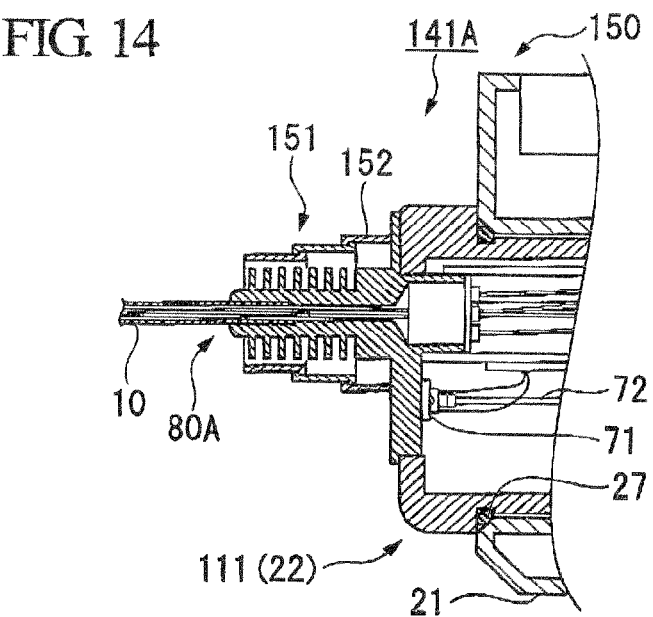
FIG. 14 is a partial cross-sectional view as seen from a side showing a main body unit of an endoscope apparatus according to a fourth embodiment of the present invention.
Figure 15:
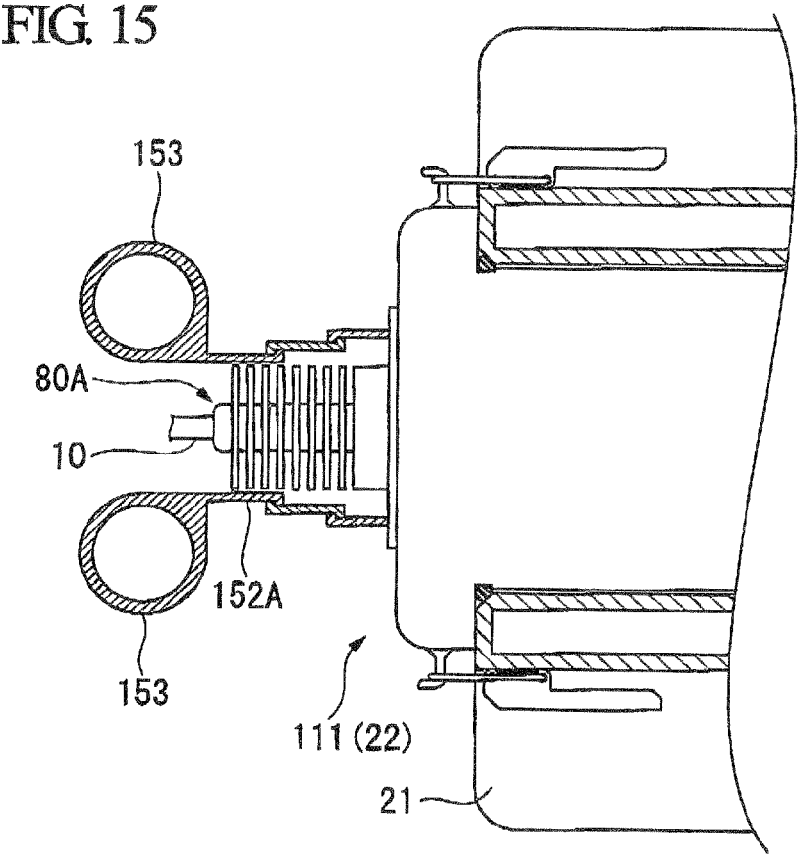
FIG. 15 is a partial bottom view showing a partial cross section of the main body unit shown in FIG. 14.

FIG. 14 is a partial cross-sectional view as seen from a side showing a main body unit 150 of the endoscope apparatus 141, while FIG. 15 is a partial bottom view showing a partial cross-section of the main body unit 150. As is shown in FIG. 14 and FIG. 15, a shielding portion 151 has a telescopic structure similar to that of the shielding portion 131. However, the thickness of tubular components 152 is set greater than that of the tubular components 132 so that an increase in strength is obtained. Moreover, as is shown in FIG. 15, annular finger grip portions 153 are provided in two locations facing each other on either side of the axis on a tubular component 152A which is located furthest on the distal end side of the insertion portion 10.

Figure 16:
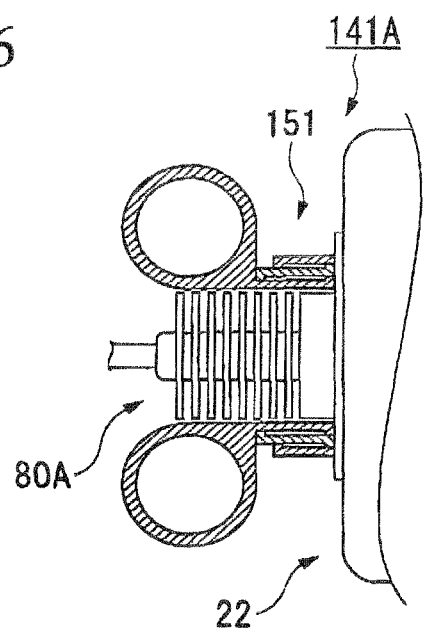
FIG. 16 is a view showing a state in which the shielding portion of the endoscope apparatus according to the fourth embodiment of the present invention is folded.

As is shown in FIG. 16, when the endoscope apparatus 141 is being used, the shielding portion 151 is folded and the heat from the heat discharge unit 80A is efficiently dispersed. When the drive unit 22 is removed from the casing portion 21 in order for it to be replaced with another unit or the like, a user inserts their fingers in the finger grip portions 153 and pulls them in a direction away from the casing portion 21. As a result, firstly the shielding portion 151 is extended towards the distal end side of the insertion portion 10, then, as is shown in FIG. 14 and FIG. 15, the periphery of the heat discharge unit 80A becomes covered by the shielding portion 151. If the finger grip portions 153 are pulled further, the engagement of the connector 26 is released, and a drive unit 22 is uncoupled from the casing portion 21.

In the endoscope apparatus 141 of the present embodiment, the periphery of the heat discharge unit 80A becomes covered by the shielding portion 151 in conjunction with the operation to pull the finger grip portions 153 when the drive unit 22 is being removed. As a result of this, any accidental contact by a portion of a user's body with the heat discharge unit 80A is inhibited. Accordingly, it is possible to replace an insertion portion unit or the like both easily and safely without having to pay any special attention to the heat discharge unit 80A, and an endoscope apparatus which is easy to use is obtained.

Figure 17:
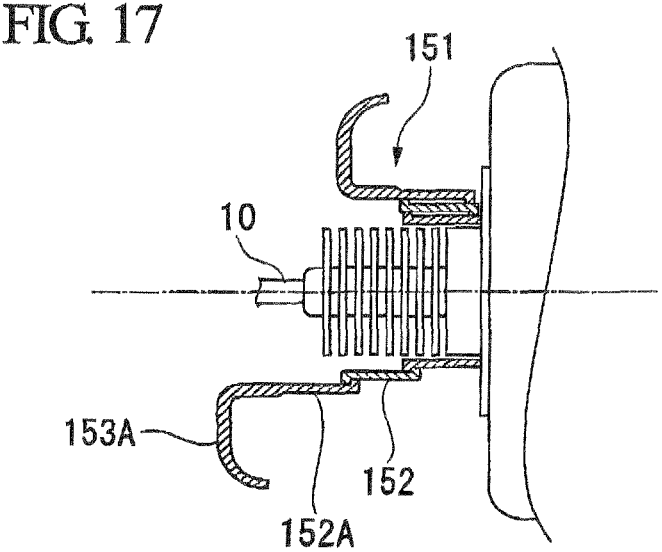
FIG. 17 is a view showing another embodiment of the shielding portion according to the fourth embodiment of the present invention.

In the shielding portion 151 of the present embodiment as well, as in the variant example shown in FIG. 17, it is also possible for the plurality of tubular components 152 to be arranged in a sequence in which their diameter becomes smaller moving inwards from the distal end side of the insertion portion 10. Moreover, the shape of the finger grip portions is not limited to a ring shape, and hook-shaped finger grip portions 153A such as those shown in FIG. 17 may also be used.

Moreover, when the drive unit 22 is separated from the casing portion 21, the heavy outer packaging 111 side tends to move downwards, and a considerable force is applied to the connecting portion between the tubular component 152A and the finger grip portions. In order to properly avoid this condition, it is also possible for the finger grip portions 153 and the like to be mounted such that they are able to pivot on a plane which is parallel to the connecting portion on the outer circumferential surface of the tubular component 152A by means of a pivot shaft or the like.

Next, a fifth embodiment of the present invention will be described with reference made to FIG. 18 through FIG. 20. The structure of an endoscope apparatus 161 of the present embodiment differs from the structures of the endoscope apparatuses of the above described respective embodiments in the configuration of the shielding portion.

Figure 18:
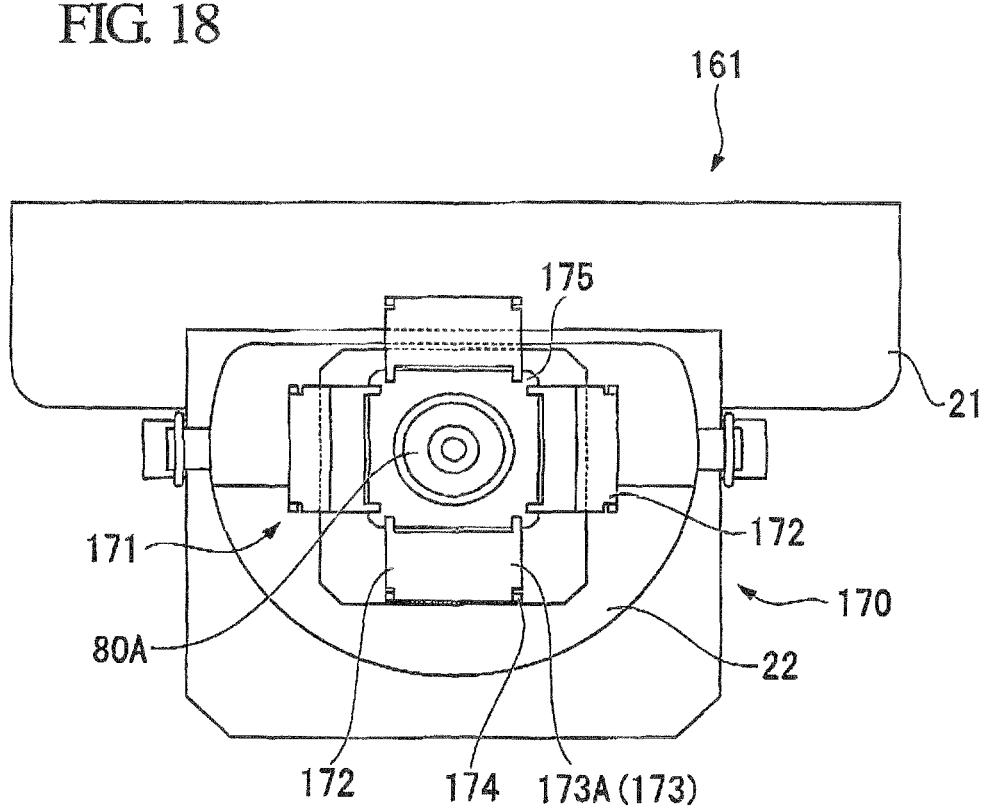
FIG. 18 is a front view of a main body unit of an endoscope apparatus according to a fifth embodiment of the present invention.
Figure 19:
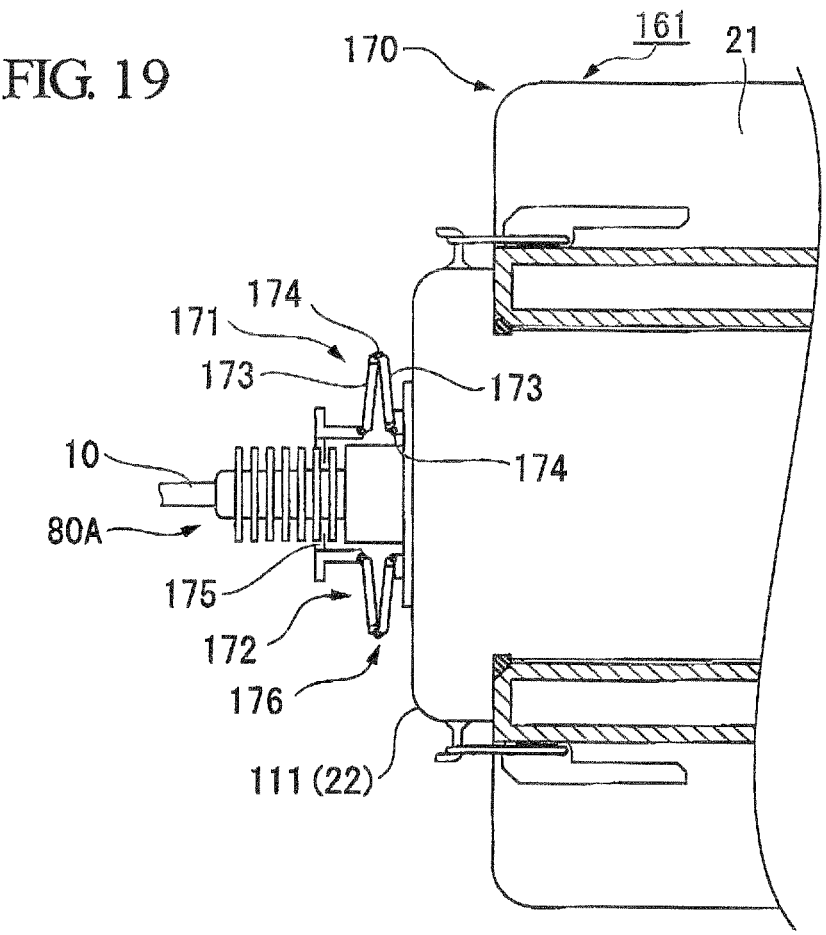
FIG. 19 is a partial bottom view showing a partial cross section of the main body unit shown in FIG. 18.

FIG. 18 is a front view of a main body unit 170 of the endoscope apparatus 161, while FIG. 19 is a partial bottom view showing a partial cross-section of the main body unit 170. As is shown in FIG. 18 and FIG. 19, a shielding portion 171 is provided instead of the shielding portion 25 in the endoscope apparatus 161.

The shielding portion 171 is provided with four retractable portions 172 that are able to expand and retract in the axial direction of the insertion portion 10.

Each retractable portion 172 is formed by connecting together a plurality of plate shaped components 173 that are formed from resin or the like such that they are able to pivot round each other by means of a plurality of pivot shafts 174.

As is shown in FIG. 18, the four retractable portions 172 are mounted respectively at four locations above and below and to the left and right of the heat discharge unit 80A. Four plate-shaped components 173A that are positioned closest to the distal end side of the insertion portion 10 in each retractable portion 172 are each pivotably mounted on a frame body 175. Accordingly, by moving the frame body 175 in the axial direction of the insertion portion 10, the four retractable portions 172 can be expanded or retracted as a single unit.

Operations when the endoscope apparatus 161 of the present embodiment which has the above described structure is put to use will now be described.

In the present embodiment, when the endoscope apparatus 161 is being used, as is shown in FIG. 19, each retractable portion 172 of the shielding portion is retracted in the axial direction of the insertion portion 10 so that the heat discharge unit 80A is left exposed. By employing this structure, the heat from the heat discharge unit 80A is efficiently dispersed.

When the drive unit 22 is being switched or the like, of those portions making up the respective retractable portions 172 which have been placed in a retracted state, a user presses protruding portions 176 that protrude in a direction away from the axis of the insertion portion 10 towards the axis of the insertion portion 10.

At this time, the user may also press the protruding portions 176 in two mutually opposing locations on either side of the axis of the insertion portion 10 towards each other.

Figure 20:
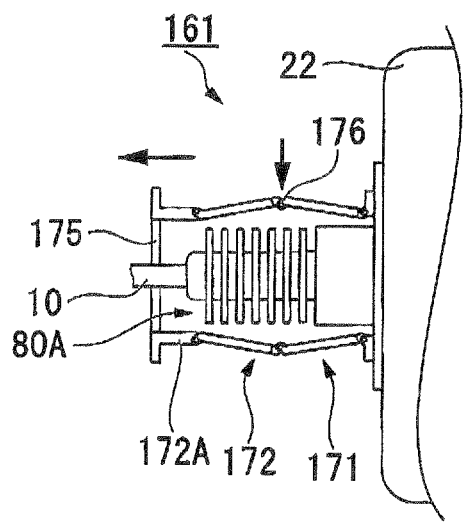
FIG. 20 is a view showing an operation when the endoscope apparatus according to the fourth embodiment of the present invention is in use.

As is shown in FIG. 20, when the protruding portions 176 are pressed in, the retractable portions 172 are made to extend towards the distal end side of the insertion portion 10. At this time, because the frame body 175 that is mounted on the plate shaped components 173A of the extended retractable portions moves towards the distal end side of the insertion portion 10, all of the four retractable portions 172 extend in synchronization with each other towards the distal end side of the insertion portion 10. As a result, the top and bottom and the left and right of the heat discharge unit 80A become covered by the shielding portion 171, and any contact by a portion of a user's body with the heat discharge unit 80A is inhibited.

In the endoscope apparatus 161 of the present embodiment as well, the heat discharge unit 80A is suitably inhibited from coining into contact with a portion of a user's body by the shielding portion 171, and an endoscope apparatus which is easy to use is obtained.

Moreover, the only components that are able to move when the shielding portion 171 is being expanded or contracted are the pivot shafts 174 in the protruding portions 176 of each retractable portion 172. Because of this, compared with the shielding portions having the telescopic structures described above, it is possible to switch the shape of the shielding portion smoothly and with fewer operations between a shielded state and an radiation state.

In the present embodiment, an example is described in which four retractable portions 172 are mounted above and below and to the left and right of the heat discharge unit 80A. However, the placement positions of the retractable portions are not limited to this, and they may also be mounted so as to form angles with the four up, down, left, and right directions. Moreover, it is also possible to change the design so that the retractable portions are provided in three directions and no bottom retractable portion is provided.

Furthermore, as in the fourth embodiment, it is also possible for finger grip portions to be provided in the plate shaped components 173A that are positioned furthest on the distal end side of the insertion portion 10.

The respective embodiments of the present invention have been described above, however, the range of technology of the present invention is not limited to the above described embodiments and various modifications may be made insofar as they do not depart from the spirit or scope of the present invention.

For example, in each of the above described embodiment, an example is described in which the casing portion and drive unit are freely detachable in the main body unit. However, this structure is not essential in the endoscope apparatus of the present invention and it is also possible for the casing portion and drive unit to not be detachable from each other. However, if the casing portion and drive unit are freely detachable, the possibility that a portion of the body of a user will make contact with the heat discharge unit when the drive unit is being attached or removed is increased. Because of this, the structure of the endoscope apparatus of the present invention, in particular, has considerable merit.

Moreover, in each of the above described embodiments, an example is described in which the light emitting component of the light source section is an LED. However, in addition to these examples, it is also possible to selectively use, as is appropriate, various types of known structures such as, for example, various types of lamp and light emitting elements such as laser diodes (LD) and the like.

Furthermore, because the installation position of the heat discharge unit is not restricted to the base end of the insertion portion, the installation position of the shielding portion can also be suitably set in accordance with the position of the heat discharge unit.

Note that the structures and configurations and the like in each of the above described embodiments can also be combined as is appropriate.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as limited by the foregoing description and is only limited by the scope of the appended claims.

What is claimed is:

1. An endoscope apparatus comprising:
an insertion portion;
an observation device provided at a distal end of the insertion portion;
an illumination unit provided at the distal end of the insertion portion, the illumination unit being configured to illuminate a visual field of the observation device;
an outer packaging provided at a proximal end of the insertion portion;
a light emitting component provided in the outer packaging;
a light guide configured to guide light emitted by the light emitting component to the illumination unit;
a heat discharge unit including a first portion which is disposed in the outer packaging and is thermally connected to the light emitting component, and a second portion which comprises a fin, extends from the first portion, and is disposed outside the outer packaging; and
a shielding portion extending from the outer packaging toward outside of the outer packaging, the shielding portion being integrally formed with the outer packaging, the shielding portion being disposed around the second portion of the heat discharge unit and separated from the second portion of the heat discharge unit, and the shielding portion covering a part of the second portion of the heat discharge unit,
wherein both the outer packaging and the shielding portion are formed from resin.

2. The endoscope apparatus according to claim 1, wherein the shielding portion includes:
a top plate portion disposed above the second portion of the heat discharge unit; and
a side wall portion disposed lateral to the second portion of the heat discharge unit.

3. The endoscope apparatus according to claim 2, wherein a through hole is formed in the top plate portion.

4. The endoscope apparatus according to claim 3, wherein the through hole is sized so as to prevent a finger of a user from being inserted into the through hole.

5. The endoscope apparatus according to claim 1, wherein the endoscope apparatus comprises:
- an insertion portion unit including the insertion portion, the observation device, the illumination unit, the outer packaging, the light emitting component, the light guide, the heat discharge unit, and the shielding portion; and
- a main body unit including a display unit and a holding portion, wherein the insertion portion unit is detachably coupled to the main body unit.

6. The endoscope apparatus according to claim 1, wherein the shielding portion leaves a part of the second portion of the heat discharge unit exposed.

7. The endoscope apparatus according to claim 6, wherein the shielding portion includes:
- a top plate portion disposed above the second portion of the heat discharge unit; and
- side wall portions disposed lateral to the second portion of the heat discharge unit;
- wherein a bottom of the second portion of the heat discharge unit is exposed.

8. The endoscope apparatus according to claim 7, wherein a through hole is formed in the top plate portion.

* * * * *